United States Patent
Toon et al.

(10) Patent No.: US 10,450,544 B2
(45) Date of Patent: Oct. 22, 2019

(54) METHODS OF PRODUCING VIRUSES

(71) Applicant: BENCHMARK ANIMAL HEALTH LIMITED, Sheffield South Yorkshire (GB)

(72) Inventors: Lindsey Ann Toon, Aylesbury (GB); Ralf Hoffmann, Braintree (GB)

(73) Assignee: Benchmark Animal Health Limited (GB)

( * ) Notice: Subject to any disclaimer, the term of this patent is extended or adjusted under 35 U.S.C. 154(b) by 0 days.

(21) Appl. No.: 16/074,501

(22) PCT Filed: Feb. 2, 2017

(86) PCT No.: PCT/GB2017/050259
§ 371 (c)(1),
(2) Date: Aug. 1, 2018

(87) PCT Pub. No.: WO2017/134441
PCT Pub. Date: Aug. 10, 2017

(65) Prior Publication Data
US 2019/0040354 A1    Feb. 7, 2019

(30) Foreign Application Priority Data

Feb. 2, 2016   (GB) .................................. 1601861.6
Nov. 3, 2016   (GB) .................................. 1618549.8

(51) Int. Cl.
| | | |
|---|---|---|
| *C12M 1/00* | (2006.01) | |
| *A61K 39/00* | (2006.01) | |
| *C12M 1/12* | (2006.01) | |
| *C12M 1/34* | (2006.01) | |
| *C12M 3/00* | (2006.01) | |
| *C12N 5/071* | (2010.01) | |

(52) U.S. Cl.
CPC ........ *C12N 5/0602* (2013.01); *C12N 2510/02* (2013.01); *C12N 2700/00* (2013.01); *C12N 2720/10034* (2013.01); *C12N 2720/10051* (2013.01); *C12N 2720/10061* (2013.01); *C12N 2770/30034* (2013.01); *C12N 2770/30051* (2013.01)

(58) Field of Classification Search
CPC .......... C12N 7/00; A61K 39/12; C12M 23/14; C12M 27/16; C12M 47/10
See application file for complete search history.

(56) References Cited

FOREIGN PATENT DOCUMENTS

| | | |
|---|---|---|
| WO | WO 2004/074467 | 9/2004 |
| WO | WO 2012/078051 | 6/2012 |

OTHER PUBLICATIONS

Chen et al. "A cell line derived from Japanese Eel" (Fish Pathology, 1981, 16(3):129-137).*
International Search Report and Written Opinion prepared by the European Patent Office dated Apr. 4, 2017, for International Application No. PCT/GB2017/050259.
Chen et al. "A Cell Line Derived from Japanese Eel (*Anguilla japonica*) Ovary," Fish Pathology, 1981, vol. 16, No. 3, pp. 129-137.

* cited by examiner

*Primary Examiner* — Barry A Chestnut
(74) *Attorney, Agent, or Firm* — Sheridan Ross P.C.

(57) ABSTRACT

Methods of producing, propagating and multiplying viruses, methods of identifying the presence of a virus in a sample, specifically methods using Japanese eel cell cultures. Also provided are an isolated Japanese eel cell culture, optionally infected with a virus, vaccines comprising viruses grown according to the methods of the invention, and a kit for propagating viruses comprising the Japanese eel cell culture. The virus may be a fish virus such as nodavirus, Infectious Pancreatic Necrosis Virus (IPNV) and Salmon Pancreas Disease Virus (SPDV).

11 Claims, 2 Drawing Sheets
Specification includes a Sequence Listing.

METHODS OF PRODUCING VIRUSES

CROSS REFERENCE TO RELATED APPLICATIONS

This application is a national stage application under 35 U.S.C. 371 and claims the benefit of PCT Application No. PCT/GB2017/050259 having an international filing date of 2 Feb. 2017, which designated the United States, which PCT application claimed the benefit of the Great Britain Patent Application No. 1601861.6 filed 2 Feb. 2016 and Great Britain Patent Application No. 1618549.8 filed 3 Nov. 2016, the disclosure of each of which are incorporated herein by reference.

REFERENCE TO A SEQUENCE LISTING

This application contains a Sequence Listing submitted electronically as a text file by EFS-Web. The text file, name "P117342WO_sequence_listing.txt", has a size in bytes of 1000 bytes, and was prepared on Aug. 6, 2018. The information contained in the text file is incorporated herein by reference in its entirety pursuant to 37 CFR § 1.52(e)(5).

The present invention relates to methods for producing and propagating viruses, in particular fish viruses. The invention also relates to cell cultures for use in methods for producing and propagating viruses and to vaccines comprising viruses prepared by the methods thereof.

The industrial cultivation of fish through aquaculture is expanding dramatically. Infectious diseases caused by pathogens constitute a major problem that the industrial aquatic establishments must overcome. Fish pathogens may be fungal, protozoan, bacterial agents or viral, however it is the viral diseases that cause most concern to fish farmers, hatchery managers, and scientists because they are largely uncontrollable and can cause significant economic loss.

Fish are susceptible to a variety of viral infections and diseases, some of which include infectious pancreatic necrosis virus (IPNV), pillar cell necrosis virus (PCNV), nodavirus or viral nervous necrosis (VNN), salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anaemia virus (ISAV), as well as others in the following families: Birnaviridae; Rhabdoviridae; Iridoviridae; Reoviridae; Ortomixovirus; Paramixovirus; Arterivirus; and Picornavirus.

Developing efficacious vaccines is a solution to reducing high mortalities and economic losses encountered due to viral infections in fish. However, the cost of producing inactivated vaccines is high because it requires cultivation of viruses in bulk followed by inactivation.

Methods of vaccine manufacture known in the art include use of embryonic eggs (e.g. bird embryos), cell (tissue) cultures (TC), live animal inoculation and/or use of transgenic animals. Investigational methods using plant, insect cells or bacteria cultures are also known.

Each of these methods have their advantages and disadvantages. For example, while the production time for cell-based vaccines is significantly reduced compared to egg-based vaccines, cell-based vaccines have relatively high manufacturing costs and low yields in comparison.

Several cell cultures for the propagation of viruses are known, for example, epithelioma papulosum cyprinid (EPC), bluegill fry caudal trunk (BF-2), grouper *Epinephelus coioides* (GF-1), striped snakehead fry (SSN-1), gilt headed seabream caudal fin (SAF-1), rainbow trout gonad 2 (RTG-2), Chinook salmon embryonic (CHSE-214) and Asian grouper strain K (AGK) cells.

The present invention provides improved methods of producing and propagating viruses which overcome some of the problems in the prior art.

The first aspect of the present invention provides a method of propagating a virus comprising the steps:
infecting a suitable cell culture with the virus;
culturing the infected cell culture;
harvesting the virus; and
optionally purifying the virus,
wherein said cell culture is a Japanese eel cell culture.

In embodiments of the present invention, the cell culture may comprise a mixed cell line, i.e. a mixture of two or more cell lines, or a single cell line.

The Japanese eel cell culture may comprise a single cell type or a mixture of two or more cell types. For example, the Japanese eel cell culture may comprise an epithelial cell and/or a fibroblast cell. In some embodiments, the cell culture comprises an epithelial cell and a fibroblast cell.

Preferably the cell culture is the cell culture derived from *Anguilla japonica* designated *Anguilla japonica*-K deposited by the Applicant at the European Collection of Authenticated Cell Cultures (ECACC) under accession number 16062701.

The term "*Anguilla japonica*" (*A. japonica*) or "Japanese eel" refers to a species of anguillid eel. This is commonly found in Japan, China, Taiwan and Vietnam and is a catadromous fish, meaning that it spawns in the sea but lives partly in freshwater.

The term "*Anguilla japonica*-K" (AJK), or alternatively "*Anguilla* genus K", is the name given to the novel cell culture according to the present invention.

During the step of culturing, the infected cell culture may be incubated at a temperature of between 10 and 30° C., more preferably between 15 and 28° C. It will be appreciated that the optimum incubation temperature will depend on the type and strain of the virus that is to be propagated. For example, where the virus is IPNV, the culture temperature is preferably around 15° C. For example, where the virus is nodavirus, such as betanodavirus, the culture temperature is preferably around 28° C.

The present inventors have found that tissues collected from *Anguilla japonica* can be cultivated in vitro and unexpectedly form a viable cell culture for the production and propagation of viruses at surprisingly high yields. It was also surprising to observe that the cell culture was able to produce and propagate these unexpectedly high viral yields at lower incubation temperatures than commonly observed for other cell lines or cell cultures used in the field. For the purposes of the present invention, the cell culture has been called *Anguilla japonica*-K.

Preferably, the virus is a fish virus. A "fish virus" is any virus that is capable of causing symptoms or disease in fish.

The virus may be a RNA virus or a DNA virus.

Preferably, the virus is a RNA virus. In some embodiments, the virus is a double-stranded RNA virus. In alternative embodiments, the virus is a single-stranded RNA virus, for example a positive-sense single-stranded RNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis virus (IPNV), pillar cell necrosis virus (PCNV), nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), and infectious salmon anaemia virus (ISAV).

Preferably, the virus is one selected from the group: nodavirus; Infectious Pancreatic Necrosis virus (IPNV); and Salmon Pancreas Disease Virus (SPDV). In some embodiments, the virus may be a recombinant virus. Preferably the fish virus is capable of being propagated in the cell culture according to the present invention.

The term "recombinant virus" refers to a virus produced by recombining pieces of DNA e.g. using recombinant DNA. The recombination is effected by human intervention. The term may also refer to naturally occurring recombination between virus genomes in cell infected by more than one virus strain, e.g. by homologous crossing over of nucleic acid strands or by re-assortment of genomic segments.

Preferably, the cell culture is infected with viral stock at a multiplicity of infection (MOI) of between 0.1 and 10. In the context of the present invention, the term MOI refers to the ratio of agents (e.g. phage or more generally virus, bacteria) to the number of infection targets (e.g. cells). For example, when referring to a group of cells inoculated with virus particles, the multiplicity of infection or MOI is the ratio of the number of virus particles to the number of target cells present in a defined space. Preferably the agent is a fish virus and the target is an *Anguilla japonica*-K cell.

In some embodiments, the *Anguilla japonica*-K cells may be cultured at 30° C. with L-15 medium (Invitrogen) supplemented with 10% L-glutamine and 1 µL/mL of gentamicin, 7.5% foetal bovine serum (FBS). It will be appreciated that the culturing conditions e.g. media may vary depending on the virus that is to be propagated.

In other embodiments, the *Anguilla japonica*-K cells may be cultured at 29° C. with L-15 medium (Invitrogen) supplemented with 10% L-glutamine, 1 µL/mL of gentamicin and 7.5% foetal bovine serum (FBS). It will be appreciated that the culturing conditions e.g. media may vary depending on the virus that is to be propagated.

In a preferred embodiment, the *Anguilla japonica*-K cells may be cultured at 28° C. with L-15 medium (Invitrogen) supplemented with 10% L-glutamine, 1 µL/mL of gentamicin and 7.5% foetal bovine serum (FBS). It will be appreciated that the culturing conditions e.g. media may vary depending on the virus that is to be propagated.

In a further preferred embodiments, the *Anguilla japonica*-K cells may be cultured at 27.5° C. with L-15 medium (Invitrogen) supplemented with 10% L-glutamine, 1 µL/mL of gentamicin and 7.5% foetal bovine serum (FBS). It will be appreciated that the culturing conditions e.g. media may vary depending on the virus that is to be propagated.

Preferably, the virus is harvested at a final titre between about $2 \times 10^6$ TCID$_{50}$/ml to about $2 \times 10^{11}$ TCID$_{50}$/ml. In some embodiments, the final titre is at least about $2 \times 10^6$ TCID$_{50}$/ml. In other embodiments the final titre is at least about $2 \times 10^7$ TCID$_{50}$/ml, at least about $2 \times 10^8$ TCID$_{50}$/ml, at least about $2 \times 10^9$ TCID$_{50}$/ml or at least about $2 \times 10^{10}$ TCID$_{50}$/ml. It will be appreciated that the final titre that is harvested will depend on factors such as the virus type and strain.

The term "titre" in the context of the present invention would be understood to mean the effective concentration of virus. Titre is commonly measured in TCID$_{50}$/ml (50% Tissue Culture Infective Dose) i.e. the amount of virus required to kill 50% of infected hosts or to produce a cytopathic effect (CPE) in 50% of inoculated tissue culture cells.

The term "final titre" refers to the concentration of virus which has been harvested following full CPE by centrifugation of the suspension at for example 2500×g or more followed by recovery of the supernatant.

Preferably, the virus is harvested when a total cytopathic effect is observed in the cells. Preferably, the virus is harvested from a supernatant and/or lysed cells.

The term "cytopathic effect" or CPE in relation to a cell would be understood to mean destruction or damage of the cell caused by viral invasion causing morphological changes. By way of example the morphological changes are brought about as a consequence of viral replication which may be accompanied by accumulation of new viral particles in the cell or release of new viral particles in the supernatant.

The second aspect of the present invention provides a cell culture suitable for the production of a virus, wherein the cell culture is a Japanese eel cell culture.

The Japanese eel cell culture may comprise a single cell type or a mixture of two or more cell types. For example, the Japanese eel cell culture may comprise an epithelial cell and/or a fibroblast cell. In some embodiments, the cell culture comprises an epithelial cell and a fibroblast cell.

Preferably, the Japanese eel cell culture is the cell culture designated *Anguilla japonica*-K deposited with the European Collection of Authenticated Cell Cultures (ECACC) with accession number 16062701.

Preferably, the virus is a fish virus.

The virus may be a RNA virus or a DNA virus.

Preferably, the virus is a RNA virus. In some embodiments, the virus is a double-stranded RNA virus. In alternative embodiments, the virus is a single-stranded RNA virus, for example a positive-sense single-stranded RNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis (IPNV), pillar cell necrosis virus (PCNV), nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anaemia virus (ISAV).

Preferably, the virus may be one selected from the group: nodavirus; infectious pancreatic necrosis virus (IPNV); and salmon pancreas disease virus (SPDV). In some embodiments, the virus may be a recombinant virus. Preferably the fish virus is capable of being propagated in the cell culture according to the present invention.

The third aspect of the present invention provides use of a Japanese eel cell culture to multiply a viral stock.

The term "viral stock" would be understood by the skilled person and generally refers to a solution comprising said virus.

The Japanese eel cell culture may comprise a single cell type or a mixture of two or more cell types. For example, the Japanese eel cell culture may comprise an epithelial cell and/or a fibroblast cell. In some embodiments, the cell culture comprises an epithelial cell and a fibroblast cell.

Preferably, the Japanese eel cell culture is the cell culture designated *Anguilla japonica*-K deposited with the European Collection of Authenticated Cell Cultures (ECACC) with accession number 16062701.

Preferably, the virus is a fish virus.

The virus may be a RNA virus or a DNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis (IPNV), pillar cell necrosis virus (PCNV), Nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anemia virus (ISAV).

Preferably, the virus may be one selected from the group: nodavirus; Infectious Pancreatic Necrosis Virus (IPNV); and Salmon Pancreas Disease Virus (SPDV). In some embodiments, the virus may be a recombinant virus. Preferably the fish virus is capable of being propagated in the cell culture according to the present invention.

The fourth aspect of the present invention provides an isolated Japanese eel cell infected with a virus. The Japanese eel cell may be an epithelial cell or a fibroblast cell.

Preferably, the Japanese eel cell is from the cell culture designated *Anguilla japonica*-K deposited with the European Collection of Authenticated Cell Cultures (ECACC) with accession number 16062701.

Preferably, the virus is a fish virus.

The virus may be a RNA virus or a DNA virus.

Preferably, the virus is a RNA virus. In some embodiments, the virus is a double-stranded RNA virus. In alternative embodiments, the virus is a single-stranded RNA virus, for example a positive-sense single-stranded RNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis virus (IPNV), pillar cell necrosis virus (PCNV), nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), and infectious salmon anaemia virus (ISAV).

Preferably, the virus is one selected from the group: nodavirus; Infectious Pancreatic Necrosis virus (IPNV); and Salmon Pancreas Disease Virus (SPDV). In some embodiments, the virus may be a recombinant virus. Preferably the fish virus is capable of being propagated in the cell culture according to the present invention.

The fifth aspect of the present invention provides a vaccine comprising a virus produced by a method according to the invention, for use in the prophylaxis or treatment of disease in a fish.

Preferably, the virus is in an inactivated form.

Preferably, the virus is present at a titre greater than $1 \times 10^6$ $TCID_{50}$/ml, greater than $1 \times 10^7$ $TCID_{50}$/ml, greater than $1 \times 10^8$ $TCID_{50}$/ml, greater than $1 \times 10^9$ $TCID_{50}$/ml, or greater than $1 \times 10^{10}$ $TCID_{50}$/ml.

Cell-based vaccines have a number of advantages over egg-based vaccines which include faster production times, easy isolation of the virus and avoidance of egg-based allergy reactions. Furthermore, cell lines and cultures can be grown in synthetic media which minimises the risks associated with animal serum. However, disadvantages of cell-based methods include increased cost and reduced viral yields. The cell culture of the present invention provides improvements to existing cell-based methods for producing fish vaccines.

The sixth aspect of the present invention provides a kit for propagation of a virus, the kit comprising a Japanese eel cell culture and instructions for use.

The Japanese eel cell culture may comprise a single cell type or a mixture of two or more cell types. For example, the Japanese eel cell culture may comprise an epithelial cell and/or a fibroblast cell. In some embodiments, the cell culture comprises an epithelial cell and a fibroblast cell.

Preferably, the cell culture is the cell culture designated *Anguilla japonica*-K deposited with the European Collection of Authenticated Cell Cultures (ECACC) with accession number 16062701.

Preferably, the virus is a fish virus.

The virus may be a RNA virus or a DNA virus.

Preferably, the virus is a RNA virus. In some embodiments, the virus is a double-stranded RNA virus. In alternative embodiments, the virus is a single-stranded RNA virus, for example a positive-sense single-stranded RNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis virus (IPNV), pillar cell necrosis virus (PCNV), nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), and infectious salmon anaemia virus (ISAV).

Preferably, the virus is one selected from the group: nodavirus; Infectious Pancreatic Necrosis virus (IPNV); and Salmon Pancreas Disease Virus (SPDV). In some embodiments, the virus may be a recombinant virus. Preferably the fish virus is capable of being propagated in the cell culture according to the present invention.

The seventh aspect of the present invention provides a method of producing a virus comprising the steps:
transducing a suitable cell culture with a viral stock;
culturing the transduced cells in culture medium;
recovering the virus; and
optionally purifying the virus from the culture medium,
wherein the cell culture is a Japanese eel cell culture.

The Japanese eel cell culture may comprise a single cell type or a mixture of two or more cell types. For example, the Japanese eel cell culture may comprise an epithelial cell and/or a fibroblast cell. In some embodiments, the cell culture comprises an epithelial cell and a fibroblast cell.

Preferably the Japanese eel cell culture is the cell culture designated *Anguilla japonica*-K deposited with the European Collection of Authenticated Cell Cultures (ECACC) with accession number 16062701.

Preferably, the virus is a fish virus.

Preferably, the virus is a RNA virus. In some embodiments, the virus is a double-stranded RNA virus. In alternative embodiments, the virus is a single-stranded RNA virus, for example a positive-sense single-stranded RNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis virus (IPNV), pillar cell necrosis virus (PCNV), nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), and infectious salmon anaemia virus (ISAV).

Preferably, the virus is one selected from the group: nodavirus; Infectious Pancreatic Necrosis virus (IPNV); and Salmon Pancreas Disease Virus (SPDV). In some embodiments, the virus may be a recombinant virus. Preferably the fish virus is capable of being propagated in the cell culture according to the present invention.

Preferably, the cell culture is transduced with viral stock at a Multiplicity of Infection (MOI) of between 0.05 and 10, between 0.1 and 10 or between 0.1 and 1. It will be appreciated that the MOI will depend on factors such as the virus type and strain.

Preferably, the virus is recovered at a final titre of the virus is between about $2\times10^6$ $TCID_{50}$/ml and about $2\times10^{11}$ $TCID_{50}$/ml. In some embodiments, the final titre is at least about $2\times10^6$ $TCID_{50}$/ml. In other embodiments the final titre is at least about $2\times10^7$ $TCID_{50}$/ml, at least about $2\times10^8$ $TCID_{50}$/ml, at least about $2\times10^9$ $TCID_{50}$/ml or at least about $2\times10^{10}$ $TCID_{50}$/ml. It will be appreciated that the final titre that is harvested will depend on factors such as the virus type and strain.

Preferably, the virus is harvested when a total cytopathic effect (CPE) is observed in the cells. Preferably, the virus is harvested from a supernatant.

To the inventors' surprise, it was found that the *Anguilla japonica*-K cell culture of the present invention was able to produce higher viral yields that other known cell lines or cultures, such as SSN cells or CCH-1 cells. For example, for SPDV, a titre of $2\times10^7$ $TCID_{50}$/ml was produced by CCH-1 cells, whereas a titre of more than two orders of magnitude was produced by cells of the invention (see Example 4).

It is thought that the small size of the *Anguilla japonica*-K cells results in the observation that there a much greater number of cells per unit volume at confluence than other cell cultures. The *Anguilla japonica*-K cell culture of the present invention also grows more rapidly when compared to salmonoid cell cultures.

These factors may contribute to the high viral yields observed in the *Anguilla japonica*-K cell culture, but can only account for part of the differences in yield. Other contributing factors include the individual cell's virus carrying capacities e.g. delayed protein shutdown, delayed/lack of apoptosis.

The eighth aspect of the present invention provides a method of identifying the presence of a virus in a sample, the method comprising:
exposing a Japanese eel cell culture to the sample;
obtaining an infected cell culture;
optionally incubating the infected cell culture;
optionally isolating a virus; and
identifying the presence of the virus.

The term "sample" refers to for example bacterial, viral cells, fish cell, tissue or bodily fluid which can be obtained from any environmental source such as an animal medium that may or may not have been in contact with an animal or an artificial source such as tissue culture material. Preferably the animal is a fish.

The Japanese eel cell culture may comprise a single cell type or a mixture of two or more cell types. For example, the Japanese eel cell culture may comprise an epithelial cell and/or a fibroblast cell. In some embodiments, the cell culture comprises an epithelial cell and a fibroblast cell.

Preferably the cell culture is the cell culture designated *Anguilla japonica*-K deposited with the European Collection of Authenticated Cell Cultures (ECACC) with accession number 16062701.

The method of identifying the presence of a virus in a sample may be a method of diagnosing the presence of a virus the sample. It would be appreciated that where the sample comprises a virus, the method would further comprise the steps of infecting the Japanese eel cell culture and growing the virus in the Japanese eel cell culture.

It would be appreciated that the step of incubating may be optional, depending on the virus, e.g. whether the virus is lytic or lysogenic.

Preferably, the virus is a fish virus.

The virus may be a RNA virus or a DNA virus.

Preferably, the virus is a RNA virus. In some embodiments, the virus is a double-stranded RNA virus. In alternative embodiments, the virus is a single-stranded RNA virus, for example a positive-sense single-stranded RNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis virus (IPNV), pillar cell necrosis virus (PCNV), nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), and infectious salmon anaemia virus (ISAV).

Preferably, the virus is one selected from the group: nodavirus; Infectious Pancreatic Necrosis virus (IPNV); and Salmon Pancreas Disease Virus (SPDV). In some embodiments, the virus may be a recombinant virus. Preferably the fish virus is capable of being propagated in the cell culture according to the present invention.

In some embodiments, the identifying step comprises one selected from the group comprising, for example: polymerase chain reaction (PCR); reverse transcription polymerase chain reaction (RT-PCR), Western Blot analysis, Northern Blot analysis, Southern Blot analysis, enzyme-linked immunosorbent assay (ELISA); electrophoretic mobility shift assay (EMSA), and/or FACS analysis. These techniques and other similar wet laboratory and computer based identification and prediction tools and techniques would be known to those of skill in the field.

The ninth aspect of the present invention provides an isolated cell culture designated *Anguilla japonica*-K deposited with accession number ECACC 16062701.

The tenth aspect of the present invention provides a method of producing an immunogenic composition comprising the steps:
  providing the isolated cell culture of the present invention;
  infecting the cell culture with a virus;
  cultivating the cell culture infected with the virus; and
  harvesting the virus from the cell culture.

Preferably, the virus is a fish virus.

The virus may be a RNA virus or a DNA virus.

Preferably, the virus is a RNA virus. In some embodiments, the virus is a double-stranded RNA virus. In alternative embodiments, the virus is a single-stranded RNA virus, for example a positive-sense single-stranded RNA virus.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a family selected from the group consisting of: Nodaviridae; Birnaviridae; Togaviridae; Rhabdoviridae; Iridoviridae; Reoviridae; Ortomixovirus; Paramixovirus; Arterivirus; Picornavirus; Nimaviridae; Dicistroviridae; Parvoviridae; and Orthomyxoviridae.

The virus may be a virus of a genus selected from the group consisting of: Alphanodavirus; Betanodavirus; Aquabirnavirus; Avibirnavirus; Blosnavirus; Entomobirnavirus; Alphavirus; Rubivirus; Novirhabdovirus; Brevidensovirus; Whispovirus; Aparavirus; Brevidensovirus; and Isavirus.

The virus may be any fish virus known to the skilled person, some of which include infectious pancreatic necrosis virus (IPNV), pillar cell necrosis virus (PCNV), nodavirus, salmonid pancreatic disease virus (SPDV), infectious hematopoietic necrosis virus (IHNV), viral haemorrhagic septicaemia virus (VHSV), infectious hypodermal and hematopoietic necrosis virus (IHHNV), shrimp white spot virus (WSV), Taura syndrome virus (TSV), hepatopancreatic parvovirus (HPV), and infectious salmon anaemia virus (ISAV).

Preferably, the virus is one selected from the group: nodavirus; Infectious Pancreatic Necrosis virus (IPNV); and Salmon Pancreas Disease Virus (SPDV). In some embodiments, the virus may be a recombinant virus. Preferably the fish virus is capable of being propagated in the cell culture according to the present invention.

The present invention is described with reference to the accompanying drawings in which.

EXAMPLES

Example 1

Species Identity of the *Anguilla japonica*-K Cell Culture—Molecular Testing

Aliquots of *Anguilla japonica*-K pre-master cell seed at passage (p) 118 and *Anguilla japonica*-K master cell seed at p 121 were tested for species identity by polymerase chain reaction (PCR) and sequencing.

Materials and Methods

Figure 1:
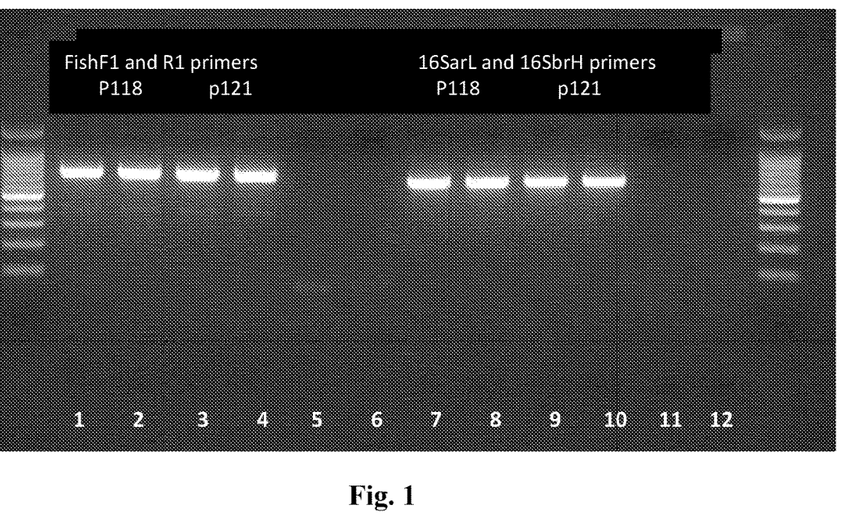
FIG. 1 shows the results of size separation by agarose gel electrophoresis of the products of PCR analysis of the *Anguilla japonica*-K cell culture deposited under ECACC accession number 16062701.

Genomic DNA was extracted from aliquots of the master cell seed p121 and pre-master cell seed p118 in duplicate using an EZ1 DNA tissue kit and EZ1 Biorobot (Qiagen) and were subjected to PCR amplification with primers for the mitochondrial cytochrome oxidase 1 (CO1) and 16S genes (Table 1 below). Products were visualised after size separation by agarose gel electrophoresis (FIG. 1). All products were excised, purified and sequenced directly by cycle sequencing (BigDye Terminator v3.1 Cycle sequencing kit and ABI 3130xl Avant genetic analyser (Applied Biosystems)). The consensus sequences from the duplicate analyses were compared to published sequences available in GenBank and EMBL by BlastN analysis.

TABLE 1

| Gene | Fragment size | Name | Primer sequences |
|---|---|---|---|
| CO1 | <650 bp | FishF1 | 5'-TCAACCAACCACAAAGACATTGGCAC-3' |
|  |  | FishR1 | 5'-TAGACTTCTGGGTGGCCAAAGAATCA-3' |
| 16S | <410 bp | 16SarL | 5'-CGCCTGTTTATCAAAAACAT-3' |
|  |  | 16SbrH | 5'-CCGGTCTGAACTCAGATCACGT-3' |

Results

FIG. 1 shows the Amplification products for CO1 gene (left hand set, lanes 1-4) and 16S gene (right hand set, lanes 7-10) of pre master *Anguilla japonica*-K cell seed p118 (1&2 and 7&8 and master cell p121 (3&4 and 9&10). Lanes 5, 6, 11 and 12 are negative controls.

PCR and sequencing of the CO1 and 16S genes of aliquots of pre-master cell seed at p118 and master cell seed at p121 all show 100% identity to the respective genes of Japanese eel (*Anguilla japonica*). There was no evidence of mixed sequence.

The *Anguilla japonica*-K cell culture is of *A. japonica* origin.

Example 2

Propagation of *Anguilla japonica*-K Cells

Methods and experimental protocols for growing cells and cell cultures would be known to persons skilled in the art. Some examples of methods according to the present invention are described below.

Cell Storage Conditions

The cell culture was stored in 50/50 by volume of 10% DMSO in Minimal Essential Medium (MEM) and Foetal Bovine Serum (FBS) undiluted, at a density of $2 \times 10^6$ cells/ml.

Cell Culture Conditions

*Anguilla japonica*-K cells were generally maintained at 28° C. with L-15 medium (Invitrogen) supplemented with 10% L-glutamine and 1 µL/mL of gentamicin, and 7.5% Foetal Bovine Serum (FBS).

Alternatively, the *Anguilla japonica*-K cells were maintained at between 15 and 28° C. in Minimal Essential Medium (MEM), 7.5% Foetal Bovine Serum (FBS), 0.5% sodium bicarbonate, and 1% L-alanyl-L-Glutamine dipeptide (Glutamax).

*Anguilla japonica*-K cells infected with IPN were maintained at 15° C. *Anguilla japonica*-K cells infected with nodavirus were maintained at 28° C.

Passage

The cells were passaged at a seeding ratio of 1:6, or cell seeding rate of $1.6 \times 10^4$ cell/cm².

Example 3

*Anguilla japonica*-K Cell Culture, ECACC Accession Number 16062701

The *Anguilla japonica*-K cell culture deposited with the ECACC relates to a sample of the pre-master cell seed at passage (p) 124. Analysis showed the cell culture to be mainly epithelial, with fibroblasts present.

Example 4

Assessment of Viral Yields

Approximately 80% confluent *Anguilla Japonica*-K cells maintained in L15 media with 2% FBS and at a density of $6 \times 10^4$ cells/cm² were inoculated with a virus (Infectious Pancreatic Necrosis (IPN), Salmon Pancreas Disease Virus (SPDV) or Nodavirus), followed by incubation at 15° C.

The cells were inoculated at a MOI of 1.0 for IPN and SPDV, and MOI's of 0.1, 0.5 and 1.0 for Nodavirus.

Figure 2:
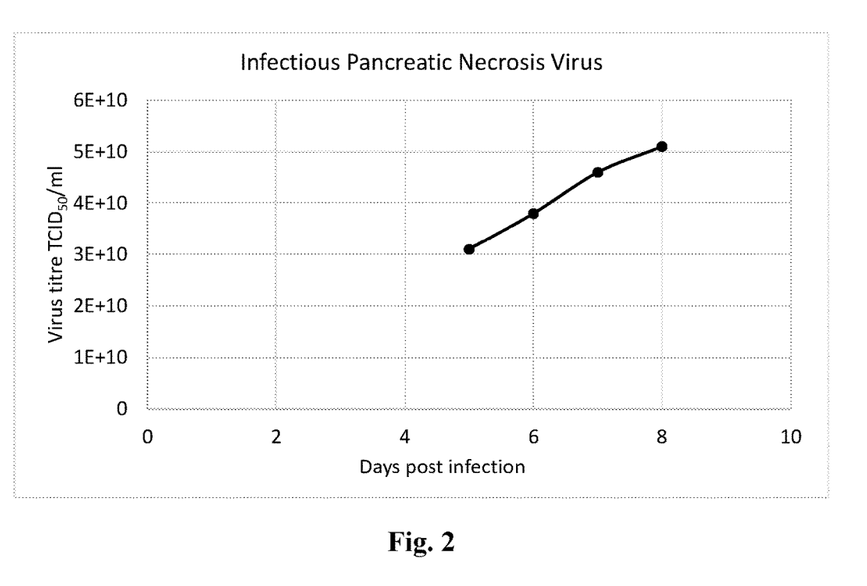
FIG. 2 is a graph showing the growth curve for Infectious Pancreatic Necrosis Virus isolate IPN NVI 015 (GenBank accession numbers AY379740 and AY379741) in *Anguilla japonica*-K cell culture (ECACC accession number 16062701) in terms of the virus titre at 5, 6, 7 and 8 days post-harvest, infected at an MOI of 1.
Figure 3:
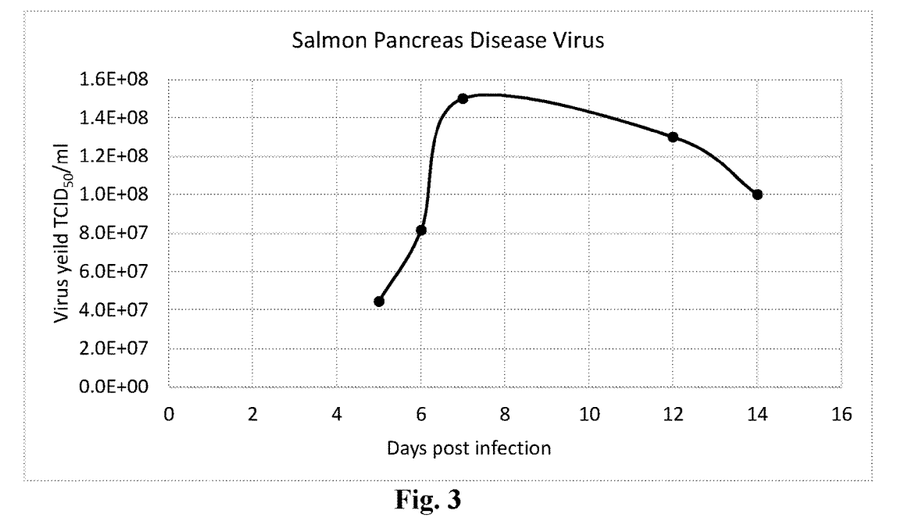
FIG. 3 is a graph showing the growth curve for Salmon Pancreas Disease Virus (SPDV) in *Anguilla japonica*-K cell culture (ECACC accession number 16062701) in terms of the virus titre at 5, 6, 7, 12 and 14 days post-harvest, infected at an MOI of 0.5.
Figure 4:
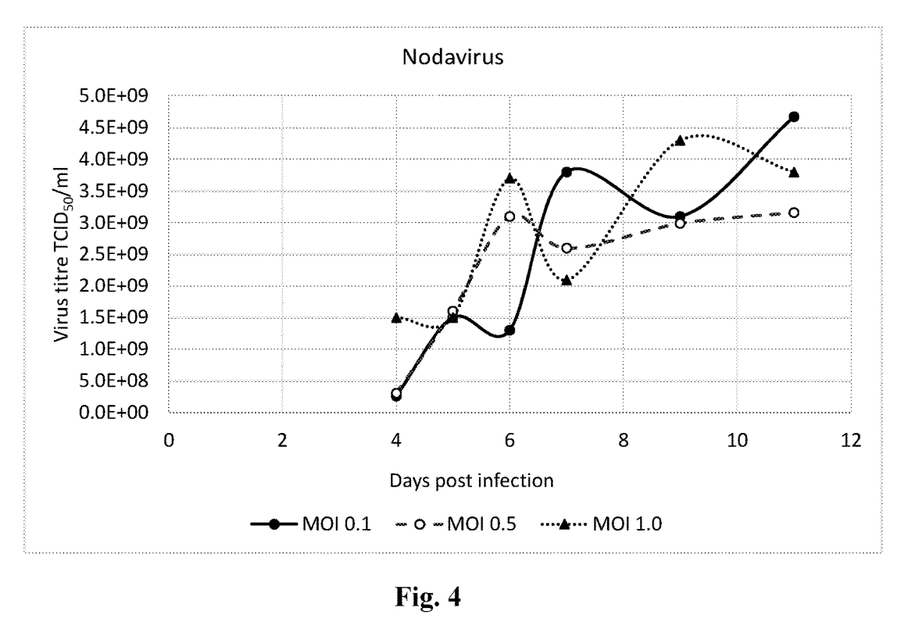
FIG. 4 is a graph showing the growth curve for Nodavirus in *Anguilla japonica*-K cell culture (ECACC accession number 16062701) in terms of the virus titre at 4, 5, 6, 7, 9 and 11 days post-harvest, infected at an MOI of 0.1, 0.5 and 1.

The growth curves for the viruses are shown in FIG. 2 (Infectious Pancreatic Necrosis Virus), FIG. 3 (Salmon Pancreatic Disease Virus) and FIG. 4 (Nodavirus).

Larger scale productions of the three viruses (IPN, SPDV and Nodavirus) in cell factories were also assessed and the virus titres at optimal harvest times were recorded. Cells were infection at an MOI of 1 for IPN, an MOI of 0.5 for SPDV and an MOI of 0.1 for Nodavirus.

The virus was harvested following full CPE by centrifugation of the suspension at 2500×g followed by recovery of the supernatant. The average titres of the viruses are shown in Table 2 below.

TABLE 2

| Virus grown in Anguilla japonica-K cells | Average titre ($TCID_{50}$/ml) at optimal harvest time over several research scale batches (cell factories) | Number of batches (cell factories) | Optimal harvest time in days post-infection (days) |
| --- | --- | --- | --- |
| SPDV | $6.6 \times 10^9$ | 5 | ~15 |
| Nodavirus | $4.65 \times 10^{10}$ | 2 | 7-11 |
| IPN | $1.58 \times 10^{10}$ | 1 | 8-12 |

The invention claimed is:

1. A method of propagating a virus comprising the steps:
   infecting a cell culture with the virus;
   culturing the infected cell culture;
   harvesting the virus; and
   optionally purifying the virus,
   wherein said cell culture is the cell culture Designated *Anguilla japonica*-K deposited with accession number 16062701.

2. The method according to claim 1, wherein the virus is a fish virus.

3. The method according to claim 1, wherein the virus is one selected from the group consisting of: nodavirus; Infectious Pancreatic Necrosis Virus (IPNV); and Salmon Pancreas Disease Virus (SPDV).

4. The method according to claim 1, wherein the cell culture is infected with viral stock at a Multiplicity of Infection (MOI) of between 0.1 and 10.

5. The method according to claim 1, wherein the virus is harvested at a final titre of the between about $2 \times 10^6$ $TCID_{50}$/ml and about $2 \times 10^{11}$ $TCID_{50}$/ml.

6. The method according to claim 1, wherein the virus is harvested when a cytopathic effect (CPE) is observed in the cells.

7. The method according to claim 1, wherein the virus is harvested from a supernatant and/or lysed cells.

8. An isolated Japanese eel cell from the cell culture designated *Anguilla japonica*-K deposited with accession number 16062701 infected with a virus.

9. The isolated Japanese eel cell according to claim 8, wherein the Japanese eel cell is from the cell culture designated *Anguilla japonica*-K deposited with accession number 16062701.

10. An isolated Japanese eel cell according to claim 8, wherein the virus is one selected from the group consisting of: nodavirus; Infectious Pancreatic Necrosis Virus (IPNV); and Salmon Pancreas Disease Virus (SPDV).

11. An isolated cell culture designated *Anguilla japonica*-K deposited with accession number ECACC 16062701.

* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: FishF1

<400> SEQUENCE: 1
tcaaccaacc acaaagacat tggcac                                        26

<210> SEQ ID NO 2
<211> LENGTH: 26
<212> TYPE: DNA
<213> ORGANISM: Artificial Sequence
<220> FEATURE:
<223> OTHER INFORMATION: FishR1

<400> SEQUENCE: 2
tagacttctg ggtggccaaa gaatca                                        26

<210> SEQ ID NO 3
<211> LENGTH: 20
<212> TYPE: DNA
<213> ORGANISM: Artificial Sequence
<220> FEATURE:
<223> OTHER INFORMATION: 16SSarL

<400> SEQUENCE: 3
cgcctgttta tcaaaaacat                                               20

<210> SEQ ID NO 4
<211> LENGTH: 22
<212> TYPE: DNA
<213> ORGANISM: Artificial Sequence
<220> FEATURE:
<223> OTHER INFORMATION: 16SbrH

<400> SEQUENCE: 4
ccggtctgaa ctcagatcac gt                                            22